US006011148A

United States Patent [19]
Bussey et al.

[11] Patent Number: 6,011,148
[45] Date of Patent: Jan. 4, 2000

[54] METHODS FOR PURIFYING NUCLEIC ACIDS

[75] Inventors: Lee B. Bussey, San Mateo; Robert Adamson, Oakland; Alan Atchley, San Franciso, all of Calif.

[73] Assignee: Megabios Corporation, Burlingame, Calif.

[21] Appl. No.: 08/691,090

[22] Filed: Aug. 1, 1996

[51] Int. Cl.[7] ............................... C07H 1/06; C12P 19/34
[52] U.S. Cl. ......................................... 536/25.4; 435/91.1
[58] Field of Search .......................... 536/25.4; 435/91.1

[56] References Cited

U.S. PATENT DOCUMENTS 4,623,723 11/1986 Keller et al. .
4,780,210 10/1988 Hsia .
5,561,064 10/1996 Marquet et al. ...................... 435/320.1

FOREIGN PATENT DOCUMENTS 0431905 6/1991 European Pat. Off. .
WO 87/07645 12/1986 WIPO .

OTHER PUBLICATIONS

Göbel, U. et al., "Quantitative Electroelution of Oligonucleotides and Large DNA Fragments from Gels and Purification by Electodialysis," *Journal of Biochemical and Biophysical Methods,* 14 (1987) pp. 245–260.

Marashi, F. et al., "Use of Ultrafiltration Microconcentrators in the Concentration and Desalting of DNA," *BioTechniques,* May/Jun. 1985, pp. 238–240.

Michaels, Stephen L. et al., (1995), *Separations Technology Pharmaceutical and Biotechnology Applications,* "Tangential Flow Filtration", pp. 57–194.

Davis, H. L. et al., (Jul. 1996), *BioTechniques,* vol. 21, pp. 93–99.

Thompson, John A., (1986), *BioChromatography,* vol. 1, No. 2, pp. 68–80.

Coppella, Steven J. et al., (1987), *Journal of Chromatography,* vol. 402, pp. 189–199.

Chandra, Gyan et al., (1992), *Analytical Biochemistry,* vol. 203, pp. 169–172.

Horn, Nancy A. et al., (May 1995), *Human Gene Therapy,* vol. 6, pp. 565–573.

Montbriand, Phillip M. et al., (1996), *Journal of Biotechnology,* vol. 44, pp. 43–46.

Hou, K.C. et al., (1990), *Biotechnology and Applied Biochemistry,* vol. 12, pp. 315–324.

Solum, N. O., (1973), *Thrombosis Research,* Pergamon Press, vol. 2, pp. 55–70.

Talmadge K. W. et al., (1989), *Journal of Chromatography,* vol. 476, pp. 175–185.

Weiss, A. R. et al., Sartorius Corporation, Developing Methods #7, Endotoxim Removal, "Clearance of Endotoxin from Solution by Adsorptive Filtration with Sartobind™ Membrane Adsorbers," pp. 1–7.

VanHaecke, E. et al., (1989), *Journal of Clinical Microbiology,* vol. 27, No. 12, pp. 2710–2712.

Sharma, Satish K., (1986), *Biotechnology and Applied Biochemistry,* vol. 8, pp. 5–22.

Filtron Membrane Separation Products Brochure, 1995/96, pp. 1–17.

*Primary Examiner*—Gary L. Kunz
*Attorney, Agent, or Firm*—McDonnell, Boehnen, Hulbert & Berghoff

[57] ABSTRACT

Methods are provided for producing highly purified compositions of nucleic acids by using tangential flow ultrafiltration. A scaleable process for producing pharmaceutical grade plasmid DNA, useful for gene therapy, is provided, which is efficient and avoids the use of toxic organic chemicals.

55 Claims, 6 Drawing Sheets

METHODS FOR PURIFYING NUCLEIC ACIDS

1. FIELD OF THE INVENTION

The invention relates to methods for producing high purity nucleic acids. Specifically, the invention relates to producing pharmaceutical quality nucleic acids. The invention relates In particular to methods for preparing pharmaceutical quality plasmid DNA.

2. BACKGROUND OF THE INVENTION

Since the advent of recombinant DNA, methods have developed and improved for the purification of DNA and RNA to further molecular biology research. While these methods have allowed considerable study of nucleic acids in research environments, they have not addressed issues involved in the human clinical use of purified nucleic acids such as is required for many current gene therapy protocols.

Gene therapy involves the introduction of nucleic acid into a patient's cells, which, when expressed, provide a therapeutic benefit to the patient. Examples include the introduction of an exogenous, functional gene to correct a genetic defect in a patient carrying a defective gene or to compensate for a gene that is not expressed at sufficient levels. Other examples include the introduction of mutant genes, antisense sequences or ribozymes to block a genetic function, e.g., in the treatment of viral infections or cancer.

Much of the focus in gene therapy has been on using viral vectors, especially retroviral vectors, for introducing exogenous nucleic acid into a patient's cells. To date, most of these protocols have been for ex vivo gene therapy, in which the patient's cells are first removed from the patient, genetically modified ex vivo, and then returned to the patient. The alternative to ex vivo gene therapy is in vivo gene therapy. In vivo gene therapy refers to the introduction of exogenous genetic capability directly to the patient where it is taken up by the target cells, which then express the introduced gene to produce a therapeutic product. Viral vectors have been used for in vivo gene therapy although their use is associated with a number of drawbacks, e.g. immunogenicity of the viral vector and safety concerns such as insertional mutagenesis or viral contamination.

Other means of in vivo gene delivery include the introduction of naked DNA into the target tissue of interest, or the use of lipid-mediated DNA delivery. Typically, introduction of naked DNA will be used when the exogenous genetic capability is to be introduced directly into the target tissue. By complexing with liposomes or lipids, DNA is compacted, allowing systemic delivery of the lipid/DNA complexes to various tissues of interest. See PCT patent application WO 93/25673. Lipid/DNA complexes can be targeted to particular tissues by altering the lipid composition, lipid/DNA ratio, mode of delivery, etc.

For any application in which nucleic acid is introduced into a patient, there is a need to produce highly purified, pharmaceutical grade nucleic acid. Such purified nucleic acid must meet drug quality standards of safety, potency and efficacy. In addition, it is desirable to have a scaleable process that can be used to produce large quantities of DNA, e.g., in the range of 100of milligrams to 100s of grams. Thus, it is desirable to have a process for producing highly pure nucleic acid that does not use toxic chemicals, known mutagens, organic solvents, or other reagents that would compromise the safety or efficacy of the resulting nucleic acid, or make scale-up difficult or impractical. It is also desirable to prepare nucleic acids free from contaminating endotoxins, which if administered to a patient could elicit a toxic response. Removal of contaminating endotoxins is particularly important where the nucleic acid is purified from gram negative bacterial sources, e.g. plasmid or bacteriophage DNA, which have high levels of endotoxins.

The invention described below meets these needs and provides other related advantages as well.

3. RELEVANT LITERATURE

Lis et al., (1975) *Nucleic Acids Res.* 2: 383–389 describe polyethylene glycol-based DNA purification methods. Zasloff et al., (1978) *Nucleic Acids Res.* 5: 1139–1153 describe acid phenol purification of plasmid DNA. Sambrook et al., (1989) *Molecular Cloning: A Laboratory Manual,* 2d ed., Cold Spring Harbor Laboratory Press, describe several different methods for relatively small scale, research grade methods of plasmid DNA purification. Ausubel et al., eds. (1989) *Current Protocols in Molecular Biology,* John Wiley & Sons, New York, also disclose different methods for relatively small scale methods for purifying plasmid DNA for research use.

Chandra et al., (1992) *Anal. Biochem.* 203: 169–172 describe the use of Hi-Load Q Sepharose column chromatography for preparing plasmid DNA. Marquet et al., (1995) BioPhann September 1995: 26–37 and Horn et al., (1995) *Hum. Gene Therapy* 6: 565–573 discuss process development issues and techniques including the use of polyethylene glycol and gel filtration/size exclusion chromatography to prepare plasmid DNA. Davis et al., (1996) *BioTechniques* 21: 92–99 compares cesium chloride and anion-exchange purified plasmid DNA for gene transfer efficiency. High performance liquid chromatography using anion-exchange chromatography resins to purify plasmid DNA are described in Thompson (1986) *BioChromatography* 1(2): 68–80 and Coppella, et al., (1987) *J. Chromatography* 402: 189–199.

Principles, theory and devices used for tangential flow filtration are described in Michaels et al., "Tangential Flow Filtration" in *Separations Technology, Pharmaceutical and Biotechnology Applications,* W. P. Olson, ed., Interpharm Press, Inc., Buffalo Grove, Ill. (1995). Procedures for removing endotoxin from biological samples are described in Sharma, (1986) Biotech. and Applied Biochem. 8: 5–22; Vanhaecke et al., (1989) *J. Clin. Microbiol.* 27(12): 2710–2712; Weiss et al., Sartorius Corporation, Developing Methods #7, "Endotoxin Removal," Edgewood, N.Y.; Talmadge et al., (1989) *J. Chromatography* 476: 175–185; and Hou et al., (1990) *Biotech. and Applied Biochem.* 12: 315–324. Montbriand et al., (1996) *J. Biotechnology* 44: 43–46, describe removal of endotoxin from DNA using polymyxin B resin.

All of the references cited herein are hereby incorporated by reference as if set forth in their entirety herein.

SUMMARY OF THE INVENTION

The present invention is directed to a method for purifying a nucleic acid from a solution comprising the nucleic acid, the method comprising the steps of:
a) circulating the solution through an ultrafiltration unit under conditions sufficient to allow a gel layer to form;
b) filtering the solution through the ultrafiltration unit comprising a gel layer to provide a permeate solution and a retentate solution whereby the nucleic acid is retained in the retentate solution;
c) collecting the retentate solution to provide a purified nucleic acid solution.

In preferred embodiments, the nucleic acid is DNA, particularly viral or plasmid DNA. The ultrafiltration unit is preferably an open-channel, flat plate device. In further preferred embodiments, the ultrafiltration membrane has a molecular weight cut-off of between 1 K and 1,000 K, most preferably around 300 K. The method preferably includes preparing the gel layer using pressure of from about 5 psi to about 30 psi, preferably around 10 to 15 psi. The nucleic acid solution may be concentrated in the range of about 2-fold to about 50-fold during the ultrafiltration step.

In additional preferred embodiments, the nucleic acid solution is further purified after tangential flow ultrafiltration by methods comprising the steps of:

d) filtering the retentate solution through a 0.2 μm filter to provide a substantially purified nucleic acid solution;

e) applying the substantially purified nucleic acid solution to a positively charged ion exchange chromatography resin wherein the nucleic acid is eluted from the ion exchange chromatography resin with a saline gradient to provide an eluted nucleic acid solution;

whereby a purified nucleic acid solution is obtained.

In a farther embodiment, the invention provides a pharmaceutical composition comprising the nucleic acid prepared according to the method of the invention. The pharmaceutical composition is preferably DNA and comprises less than about 100 endotoxin units per milligram nucleic acid, less than about 2% RNA, less than about 1% single stranded DNA, and less than about 0.1% protein. In embodiments of the invention where the pharmaceutical composition comprises plasmid DNA, the composition preferably is less than about 1% genomic DNA and more than 90% closed circular plasmid DNA.

It is an advantage of the present invention that nucleic acid is prepared without the use of organic solvents, including phenol, chloroform, ether, ethanol, isopropanol, isoamyl alcohol, n-butanol or other organic solvents. The use of such solvents pose safety and regulatory concerns due to the possibility of trace amounts in the final product. In addition, such solvents are toxic and inflammable, and pose serious risk and disposal problems if used in the quantities required for large scale purification. The purified nucleic acid of the present invention is also substantially free of contaminating endotoxin.

It is also an advantage of the present invention that nucleic acid prepared according to the inventive method is highly purified as determined by HPLC analysis. Highly purified nucleic acid is advantageous for safety reasons as well as for improving reproducibility and efficacy of processes using such nucleic acid. In particular, highly purified DNA of the present invention is advantageously used for gene delivery using lipid carriers, whereby reproducible, high transfection efficiencies are obtained.

Specific preferred embodiments of the present invention will become evident from the following more detailed description of certain preferred embodiments and the claims.

DETAILED DESCRIPTION OF THE PREFERRED EMBODIMENTS

Definitions

"Diafiltration" is a mode of operating an ultrafiltration system in which the retentate is continuously recycled and diluted with fresh wash solution to replace that removed as permeate. Diafiltration will generally provide a cleaner separation of macromolecules retained in the retentate sample while the smaller molecules pass through into the filtrate. It may also be used to perform solvent removal or buffer exchange in the same step. "Continuous diafiltration" refers to the continuous addition of fresh wash buffer as filtration takes place. "Discontinuous diafiltration" refers to the repeated steps of concentrating the sample by ultrafiltration, and rediluting with buffer.

A "gel-layer," refers to a thin gelatinous layer of biomolecules that can form on or in an ultrafiltration membrane. The gel layer is generally a cohesive, adherent layer of constant solute concentration. It usually will have some degree of hydraulic permeability depending on the nature of the solute forming the layer.

An "open channel" filter is one which does not have a screen in the feed channel. By contrast, a "screen channel" or "closed channel" is a filter that has a screen in the feed channel.

"Permeate" refers to that portion of a sample that passes through the ultrafiltration membrane, and is also termed the "filtrate."

"Retentate" refers to that portion of a sample that does not pass through the ultrafiltration membrane.

"Tangential flow" or "cross-flow" filtration refers to a filtration process in which the sample solution circulates across the top of the membrane, while applied pressure causes solute and small molecules to pass through the membrane.

"Ultrafiltration" refers to a technique to separate particles by filtration through membranes having pore sizes ranging from about 0.001 μm to about 0.05 μm. Ultrafiltration membranes typically have a molecular weight cut-off (MWCO) in the range of 1,000 to 1,000,000 daltons. The MWCO typically is defined as the molecular weight of the globular solute which is 90% retained by that membrane. See Filtron Catalog, 1995/96, p.5. The actual molecular weight of particles that pass through or are retained by a membrane will depend on the size as well as the conformation and charge of a given molecule.

It has now been found that nucleic acids can be highly purified from a mixture of substances, including proteins, cell debris, endotoxin, small degraded nucleotides, and the like, by tangential flow ultrafiltration (TFU). This technique is simple, efficient and yields very high purity nucleic acid in a single step, often on the order of 95% to 100% pure by HPLC analysis. It is also conveniently combined with diafiltration in a single step whereby the nucleic acid solution may be concentrated and/or exchanged into a different buffer solution to remove solvents, salts, and the like.

Nucleic acids that may be purified and/or concentrated according the methods described herein include DNA, RNA and chimeric DNA/RNA molecules, and may be from any biological source including eukaryotic and prokaryotic cells, or may be synthetic. Nucleic acids that may be purified include chromosomal DNA fragments, ribosomal RNA, mRNA, snRNAs, tRNA, plasmid DNA, viral RNA or DNA, synthetic oligonucleotides, ribozymes, and the like. Preferred are viral nucleic acids, and extrachromosomal DNAs. Of particular interest are plasmid DNAs encoding therapeutic genes. By "therapeutic genes" is intended to include functional genes or gene fragments which can be expressed in a suitable host cell to complement a defective or underexpressed gene in the host cell, as well as genes or gene fragments that, when expressed, inhibit or suppress the function of a gene in the host cell including, e.g., antisense sequences, ribozymes, transdominant inhibitors, and the like.

Thus, e.g., viral DNA or RNA may be purified from prokaryotic or eukaryotic viruses, in which the viral particles are initially purified from cultures or cells permissive for viral infection in accordance with conventional techniques, e.g., from bacterial, insect, yeast, plant or mammalian cell cultures. Extrachromosomal DNAs include autonomously replicating DNAs from a variety of sources including, e.g., mammalian cells (see, e.g., Yates et al., *Nature* (1985) 313:812–815; Heinzel et al., *Mol. Cell. Biol.* (1991) 11(4): 2263–2272), plant cells, yeast cells (e.g., 2 $\mu$m plasmids), and prokaryotic cells. Plasmid DNA isolated from prokaryotic cells include naturally occurring plasmids as well as recombinant plasmids encoding a gene of interest including, e.g., marker genes or therapeutic genes.

Initial preparatory purification of the nucleic acid sample before tangential flow ultrafiltration will depend on the source of the nucleic acid and the level of purity desired. Ideally, many contaminants are removed by one or more coarse purification steps before tangential flow ultrafiltration to reduce the number of contaminating particles that could foul the ultrafiltration membrane, impeding performance, and decrease the amount of any larger contaminants that would be retained with the nucleic acid. For nucleic acids obtained from biological sources, e.g. tissues and cells, including cell lines, mammalian, yeast, plant or bacterial cells, initial preparatory steps to lyse cells and remove cell components, e.g. proteins, cell walls or membranes, can be performed using conventional methods known to those of ordinary skill in the art. See, e.g., Sambrook et al., 1989; Ausubel et al., 1989. For purification of extrachromosomal DNA, such as plasmid DNA, it is desirable to use methods that do not shear chromosomal DNA, making its removal simpler and avoiding contamination with the final plasmid DNA product. Thus, for example, plasmid DNA may be isolated from bacterial sources using conventional procedures including lysis with alkali and/or detergents, e.g. SDS, NP40, Tween 20 and the like, mechanical methods, or boiling, followed by precipitation of proteins, chromosomal DNA and cell debris. (see Sambrook, et al., 1989; Carlson et al., 1995, Biotech. *Bioeng.* 48: 303–315; Hirt, 1967, *J. Mol. Biol.* 26: 365–369) For purification of extrachromosomal DNA from mammalian cells, e.g., a conventional Hirt extraction may be used. Sambrook et al., 1989; Ausubel et al., 1989. For synthetic nucleic acids, little or no pretreatment may be necessary before TFU.

If pharmaceutical grade nucleic acid is desired, it is highly preferred that the preparatory steps do not include the use of organic solvents or toxic chemicals that may raise safety and regulatory concerns. Example 1, below, exemplifies a method for producing high purity pharmaceutical grade plasmid DNA, without use of organic or toxic chemicals, using the methods of the present invention.

Figure 1:
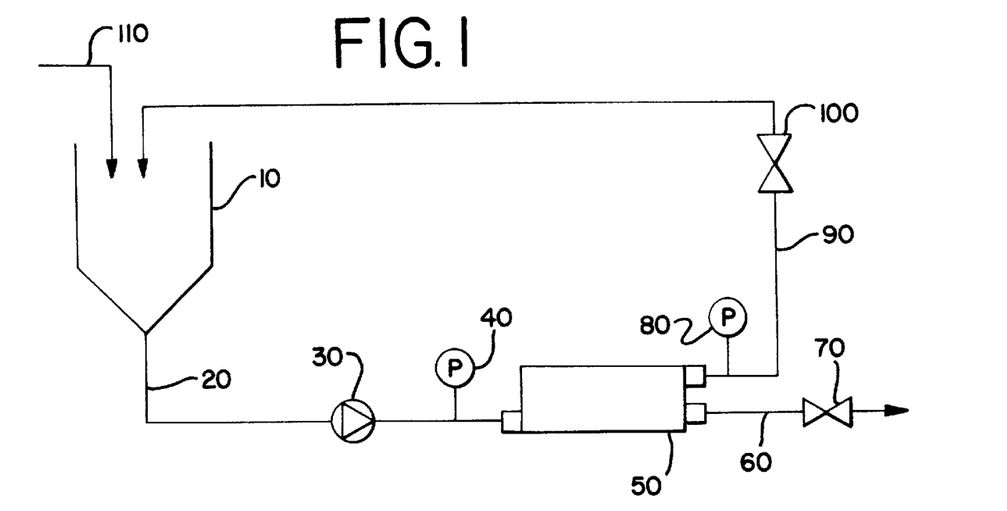
FIG. 1 is a schematic diagram of a tangential flow ultrafiltration (TFU) process.

FIG. 1 is a schematic diagram of a tangential flow ultrafiltration process. Briefly, the feed tank 10 comprises the sample solution to be filtered. The solution enters the filtration unit 50 through the feed channel or feed line 20. The circulation pump 30, located in the feed line 20 controls the solution flow. The filtration unit 50 comprises the ultrafiltration membrane, Filtration through the ultrafiltration membrane separates the sample solution into a permeate solution and a retentate solution. The permeate solution exits the unit through the permeate channel or permeate line 60. Flow through the permeate channel may be controlled through a permeate valve located in the permeate channel 60. The retentate solution passes into the retentate channel or retentate line 90, which is circulated back into the feed tank 10. Pressure across the ultrafiltration membrane (transmembrane pressure or TMP) is measured by pressure detectors in the feed channel 40 and in the retentate channel 80. TMP is controlled by adjusting the retentate valve 100. When TFU is performed in diafiltration mode, diafiltration buffer 110 is added to the sample solution in the feed tank 10. When TFU is used to concentrate the sample solution, however, diafiltration buffer 110 is not added to the feed tank 10.

The ultrafiltration membrane will be selected based on the size and conformation of the nucleic acid to be purified, and typically will have a molecular weight cut-off (MWCO) in the range of 1 K to 1,000 K daltons. For many supercoiled plasmid DNAs, ultrafiltration membranes having a MWCO around 300 K daltons may be used. For some larger plasmids, however, improved speed, purity and quality of the resultant DNA is obtained when larger MWCO membranes are used. Preferably, therefore, plasmid DNA with sizes ranging from about 2 Kb to 15 Kb are purified using ultrafiltration membranes having a MWCO of 300 K daltons; plasmids ranging from about 15 Kb to about 50 Kb may be purified using membranes having a MWCO of 500 K daltons; and plasmids of about 40 Kb or larger may be purified using membranes having a MWCO of 1,000 daltons. Under these conditions, plasmid DNA will be retained in the retentate while contaminating substances including many proteins, cell membrane debris, carbohydrates, small degraded nucleotides, etc., pass through the membrane into the filtrate. Smaller nucleic acids, e.g., small synthetic oligonucleotides, may be purified using ultrafiltration membranes with a MWCO of around 1 K to 5 K daltons. For any nucleic acid to be purified, the optimal membrane pore size may be determined empirically using small scale devices, e.g., centrifugation devices or stirred cell devices, available from a variety of commercial manufacturers. A manifold system may be used for optimizing parameters in process scale development. Commercial sources for ultrafiltration devices include Pall-Filtron (Northborough, Mass.), Millipore (Bedford, Mass.), and Amicon (Danvers, Mass.).

Many types of ultrafiltration devices useful in the present invention are commercially available including e.g., a flat plate device, spiral wound cartridge, hollow fiber, tubular or single sheet device. See Michaels et al., (1995). Preferably, the ultrafiltration unit is a flat plate device.

It has been found that shearing of the nucleic acid is minimized if the filtration device used for TFU is an open-channel device. Screened channels have been found to shear and decrease yield of the retained nucleic acid. Screen channels may be designed, however, having minimal compression of the screens such that the shearing and nucleic acid loss may be minimized.

The surface area of the ultrafiltration membrane used will depend on the amount of nucleic acid to be purified.

Generally, about five square feet of membrane is used per 200 to 400 mg nucleic acid.

The membrane may be of a low-binding material to minimize adsorptive losses, and should be durable, cleanable and chemically compatible with the buffers to be used. A number of suitable membranes are commercially available, including e.g., cellulose acetate, polysulfone, polyethersulfone and polyvinylidene difluoride. Preferably, the membrane material is polyethersulfone.

It has been found that higher yields and purities are obtained when a gel-layer is allowed to form at the membrane surface before starting TFU. Thus, the sample solution initially is circulated through the ultrafiltration device 50, with the permeate valve 70 open and the permeate solution recirculated into the feed tank 10, for sufficient time to allow a gel-layer to form. The amount of time necessary for gel-layer formation may be determined empirically by monitoring the permeate solution for product loss, e.g., by HPLC analysis. The gel-layer is adequate once the product loss into the permeate is sufficiently low. Typically, the gel layer is allowed to form for approximately 10 to 60 minutes, preferably around 15 to 30 minutes. After formation of the gel-layer, the permeate line 60 is emptied into a waste receptacle and filtration allowed to proceed.

Filtration is performed using tangential flow to circulate the sample buffer as it crosses the membrane surface. During tangential flow filtration, pressure is applied across the membrane, which allows smaller molecules to pass through the membrane while the retentate is recirculated. Typically, the flow rate is adjusted to maintain a constant transmembrane pressure. Flow rate and pressure often fluctuate initially due to the formation of a gel layer. Generally, filtration proceeds faster with higher pressures, but higher pressures are likely to cause shearing of the nucleic acid or loss due to passage through the membrane. In addition, various TFU devices may have certain pressure limitations on their operation. The pressure, therefore, may be adjusted according to the manufacturer's specification. For flat plate devices, the pressure is preferably from about 5 psi to about 30 psi, most preferably in the range of 10 psi to 15 psi. Typically, the circulation 30 is a peristaltic pump in the feed channel 20, and the pressure is controlled by adjusting the retentate valve 100.

Filtration is generally performed in diafiltration mode. Optionally, the sample solution may initially be filtered without buffer addition until concentrated to a desired volume. Once concentrated, diafiltration buffer 110 is added and filtration continues to wash the retentate solution of contaminating small molecules and remove unwanted solvents and salts. Diafiltration may be either continuous or discontinuous. Preferably, diafiltration is continuous, and performed until from about 10 to about 500 volume equivalents have been exchanged, preferably about 50 to 200 volume equivalents, and most preferably, about 100 volume equivalents are exchanged.

To further improve yield of the purified nucleic acid following TFU, the retentate solution is recirculated through the filtration unit 50, with the permeate valve 70 closed, for several minutes to remove residual nucleic acid. The retentate solution is collected, and additional diafiltration buffer 110 is added to wash the membrane filter. Typically, one to two volume equivalents of diafiltration buffer 110 are used to wash the membrane filter. The retentate is again collected and combined with the original retentate solution containing the purified nucleic acid.

Nucleic acids purified by tangential flow ultrafiltration may be used directly or may be further purified depending on the level and type of contamination in the starting sample and the desired use. Typically, the nucleic acid purified by tangential flow filtration will be greater than 90% pure, often 95% to 100% pure as analyzed by HPLC. The nucleic acid thus purified may be used for a number of applications, e.g., molecular biological applications such as cloning or gene expression, or for diagnostic applications using, e.g., PCR, RT-PCR, dendromer formation, etc.

For therapeutic uses, e.g. use in gene therapy, it may be desirable to further purify the nucleic acid obtained from the tangential flow filtration step. In a preferred embodiment of the invention, the nucleic acid sample obtained from the tangential flow filtration step is subsequently filtered through a 0.2 $\mu$m filter, further purified using ion exchange chromatography, and, optionally, filtered again through a 0.2 $\mu$m filter. Desirably, the nucleic acid is further concentrated and diafiltered using ultrafiltration, and filtered through a 0.2 $\mu$m filter as a final sterilization step.

Filtration through 0.2 $\mu$m filters can be used to remove endotoxin and microorganisms while resulting in minimal nucleic acid loss. 0.2 $\mu$m filters are available from a variety of commercial sources including, e.g., Pall-Filtron (East Hills, N.Y.), Sartorius (Edgewood, N.Y.), and Gelman (Ann Arbor, Mich.). Ideally, the filter used is one that binds endotoxin while allowing nucleic acid to pass through. Pall Ultipor® $N_{66}$® filters have been found to remove substantial endotoxin with high yield of nucleic acid. Preferably, the nucleic acid solution is pre-filtered through a 0.45 $\mu$m filter before filtration through the 0.2 $\mu$m filter. Filters made for the removal of endotoxin, e.g., ion exchange filters, in many cases are not suitable for use with nucleic acid purification because the nucleic acid will bind to the filter.

Ion exchange chromatography may be used to further purify the nucleic acid, particularly from contaminating endotoxin, trace proteins, and residual cellular contaminants. Ion exchange chromatography resins are commercially available, including from EM Separations (Gibbstown, N.J.), BioSepra (Marlborough, Mass.), Polymer Laboratories (Amherst, Mass.), Perseptive Biosystems (Cambridge, Mass.) and Pharmacia (Uppsala, Sweden). Preferred resins are those with a large pore size, e.g., greater than 3000 Å, preferably around 4000 Å; with a medium bead size, e.g., about 20 to 100 $\mu$m diameter; that do not leach matrix components. Ideally, the resin is also washable, e.g., with sodium hydroxide to allow repeated use.

A chromatography column is packed with an anion exchange chromatography resin. The optimal capacity of the column is determined empirically based on the resin used and the size of nucleic acid to be purified. The column is packed under low pressure, which will depend on the resin used, e.g., from about 0.7 bar to about 1.3 bar, preferably about 1 bar. Column pressure will be lower where resin pore size is smaller to limit trapping of the nucleic acid in the resin pores. Thus, for resins without pores, column pressure may be increased. The column is packed at about twice the anticipated flow rate in accordance with conventional techniques.

The nucleic acid sample is loaded onto the column in a loading buffer comprising a salt concentration below the concentration at which the nucleic acid would elute from the column. Typically, the salt concentration will be about 30 to 35 mS. The column will then be washed with several column volumes of buffer to remove those substances that bind weakly to the resin. Fractions are then eluted from the column using a shallow linear saline gradient according to conventional methods, e.g., using up to 1.5 M NaCl in a Tris-HCl buffer. Sample fractions are collected from the column. For large scale preparations, fractions will typically be at least 50 ml to 100 ml where the nucleic acid peak is expected, then increased in volume past the expected peak. Analytical determinations of nucleic acid yield and purity are performed on each fraction. In addition, Limulus ameobocyte lysate (LAL) analyses may be performed on each fraction to determine residual endotoxin levels in each fraction (measured as endotoxin units (EU)). Fractions containing high levels of nucleic acid and low endotoxin are pooled. The resulting nucleic acid sample may again be filtered through a 0.2 μm filter depending on the endotoxin levels and the desired purity.

For many applications it will be desirable to lower the salt concentration of the resulting nucleic acid sample, concentrate the sample, and/or exchange the buffer to a more suitable buffer for subsequent uses. A final diafiltration step may be performed at this stage to achieve that result. If desired, a smaller MWCO ultrafiltration membrane may be used for this diafiltration step than used previously for purification, since the nucleic acid will be highly purified at this stage and predominantly small solute molecules will be passed through the membrane into the filtrate. Where DNA purified according to the above protocol is to be complexed with a lipid carrier for use in gene therapy, it is desirable to exchange the DNA into a low conductivity buffer, preferably by diafiltration.

At a variety of places in the above protocol, analytical determination of nucleic acid yield and purity are advantageously performed. Typically, such assays are performed before and after each purification step, as well as to each nucleic acid-containing fraction from, e.g., preparative ion exchange chromatography. Preferred means for performing these analytical determinations include HPLC analysis of purity, spectrophotometric estimation of yield, silver staining and SDS-PAGE for protein analysis, and agarose gel electrophoresis and Southern blotting for DNA analysis.

The following Example illustrates certain aspects of the above-described method and advantageous results. The following example is shown by way of illustration and not by way of limitation.

EXAMPLE 1

Preparation of p4119 DNA

Figure 2:
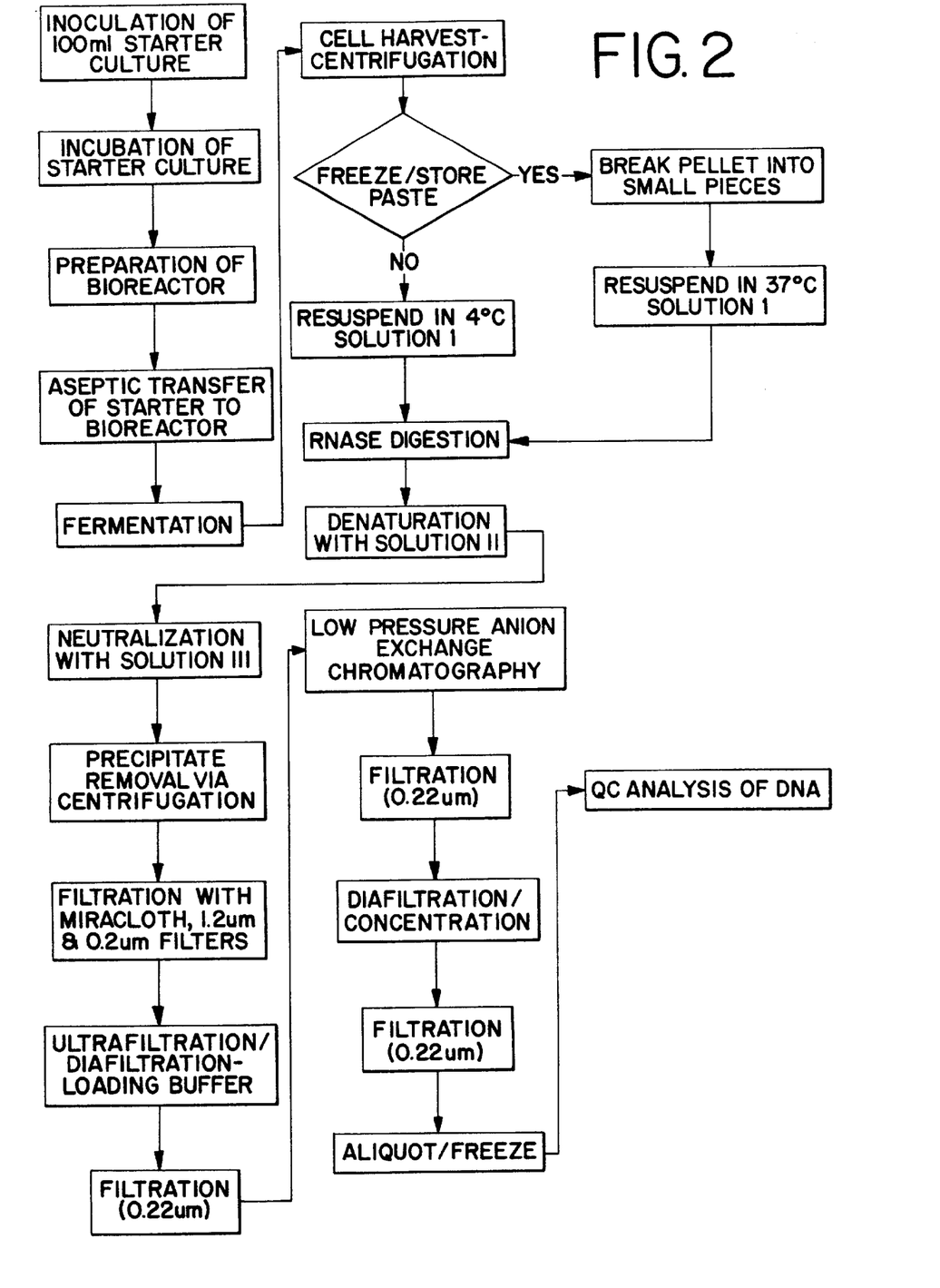
FIG. 2 illustrates a schematic diagram of large-scale plasmid DNA purification as described in Example 1.

Pharmaceutical quality DNA was prepared as follows, using aseptic culture conditions for all cell culture procedures. FIG. 2 is a schematic representation of the procedural steps.

Figure 3:
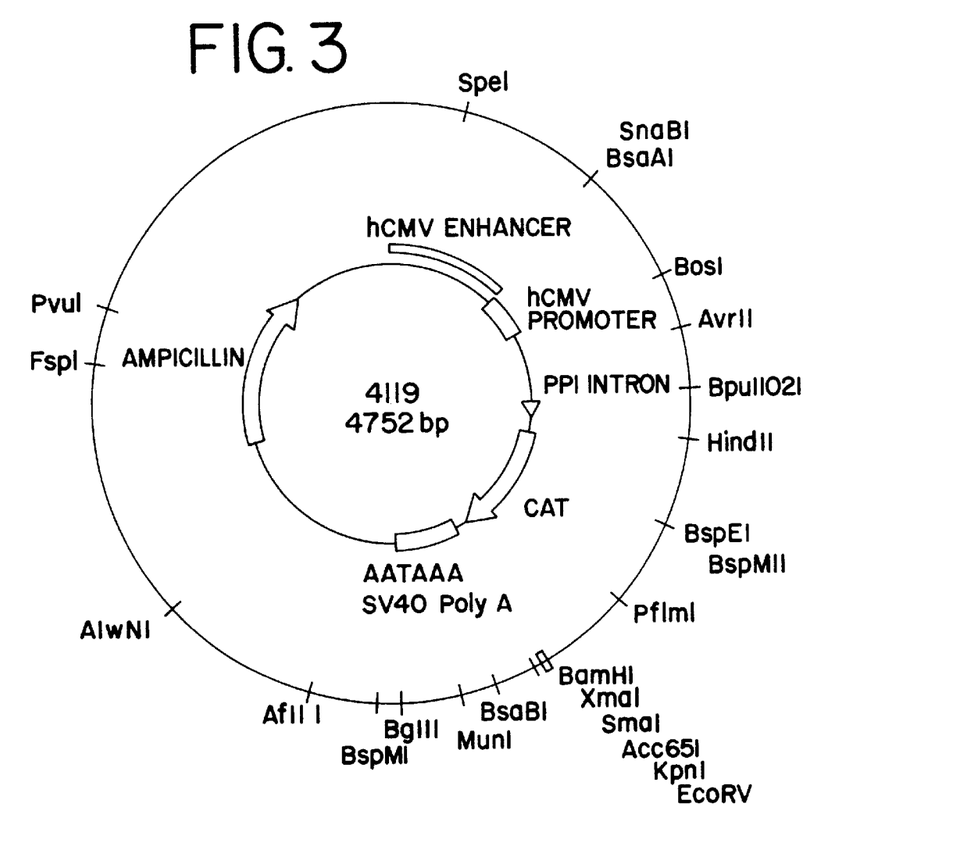
FIG. 3 is a schematic representation of the plasmid p4119.

An inoculum of *E. coli* containing plasmid p4119 (FIG. 3) was prepared from frozen stock by the addition of 1 ml of frozen (−80° C.) bacterial culture to a 500 ml foam-plugged flasks containing 100 ml TB broth (Sambrook et al., 1989) supplemented with carbenicillin (100 μg/ml). Cultures were incubated at 37° C. and shaken at 220 rpm for approximately 6 hours. Culture growth was determined by visual inspection or by determining $OD_{600}$, whereby OD values between 0.5 and 5 were deemed acceptable.

5 ml of this culture was used to inoculate each of 4 bioreactors containing 10 L TB media supplemented with carbenicillin (100 μg/ml) and with 1 ml/10 L Mazu DF204 antifoaming agent. These cultures were incubated at 37° C. and stirred initially at about 300 rpm. The cultures were aerated and dissolved oxygen was controlled via cascade control loops, agitation, airflow, and oxygen enrichment to an average of about 40% saturation. Cultures were incubated for about 10 to 16 h. After incubation, cell content of each culture was determined by $OD_{600}$; $OD_{600}$ values ranged from 16 to 18. Cells were harvested by centrifugation in a refrigerated Carr continuous flow centrifuge.

The cell pellets were spread into thin sheets and frozen at −80° C. until used for further plasmid purification. 3.2 Kg of the cell pellet was resuspended in 16 L Solution I (25 mM Tris-HCl, pH 8, 10 mM EDTA, 50 mM dextrose) at room temperature with stirring at 150 rpm for 1 h. RNase digestion was achieved by the addition of RNase (305 mg RNase/Kg cell paste) and incubating the solution on ice for 2 hrs. Cells were lysed by the addition of the cells to 32 L Solution II (0.2 N NaOH/1% SDS) in an ice bath. The solution is stirred using a Bow-Tie Stirrer (Cole Parmer, Vernon Hills, Ill.) for 25 min. This solution was then neutralized and cell debris and chromosomal DNA were precipitated by the addition of 16 L ice-cold Solution III (3 M potassium, 5 M acetate, pH 5.5). The solution was mixed with a Bow-Tie Stirrer on ice for 25 min.

The precipitated material was removed from the neutralized cell lysis solution by centrifugation. The solution was aliquotted into 1 L centrifuge bottles and centrifuged at 5300 rpm for 20 min at 2° C. The supernatants were then decanted through two layers Miracloth (CalBiochem, La Jolla, Calif.) arranged at 90° to each other, into a container at room temperature. The decanted supernatants were then filtered through 1.2 and 0.2 μm filters arranged in series.

Filtered materials were then pumped into an ultrafiltration unit and the DNA solution filtered by tangential flow filtration through a Pall-Filtron Omega open channel Centrasette unit using 25 ft² of polyethersulfone (PES) membrane having a MWCO of 300 K. The solution was introduced into the unit under a pressure of 10 psi, with the permeate channel open, and the solution allowed to circulate through the unit for about 50 min until a gel layer was formed. The permeate channel was then directed to a waste receptacle, and the DNA solution was filtered at a pressure of 10 psi until the solution was concentrated to a volume of about 3.6 L. Diafiltration buffer (Tris-HCl, pH 8.5) was then added and the solution was continuously diafiltered at a pressure of 10 psi, flow rate of about 1 L/min, until approximately 50 volume exchanges were performed.

After diafiltration, the retentate was recirculated through the ultrafilter for 10 min with the permeate valve closed. The retentate was removed and the membrane washed twice by an additional 1 L diafiltration buffer per wash for 10 min each, with the permeate valve closed. The wash solutions were added to the retentate and analyzed by HPLC and $OD_{260/280}$ analysis.

Figure 4A:
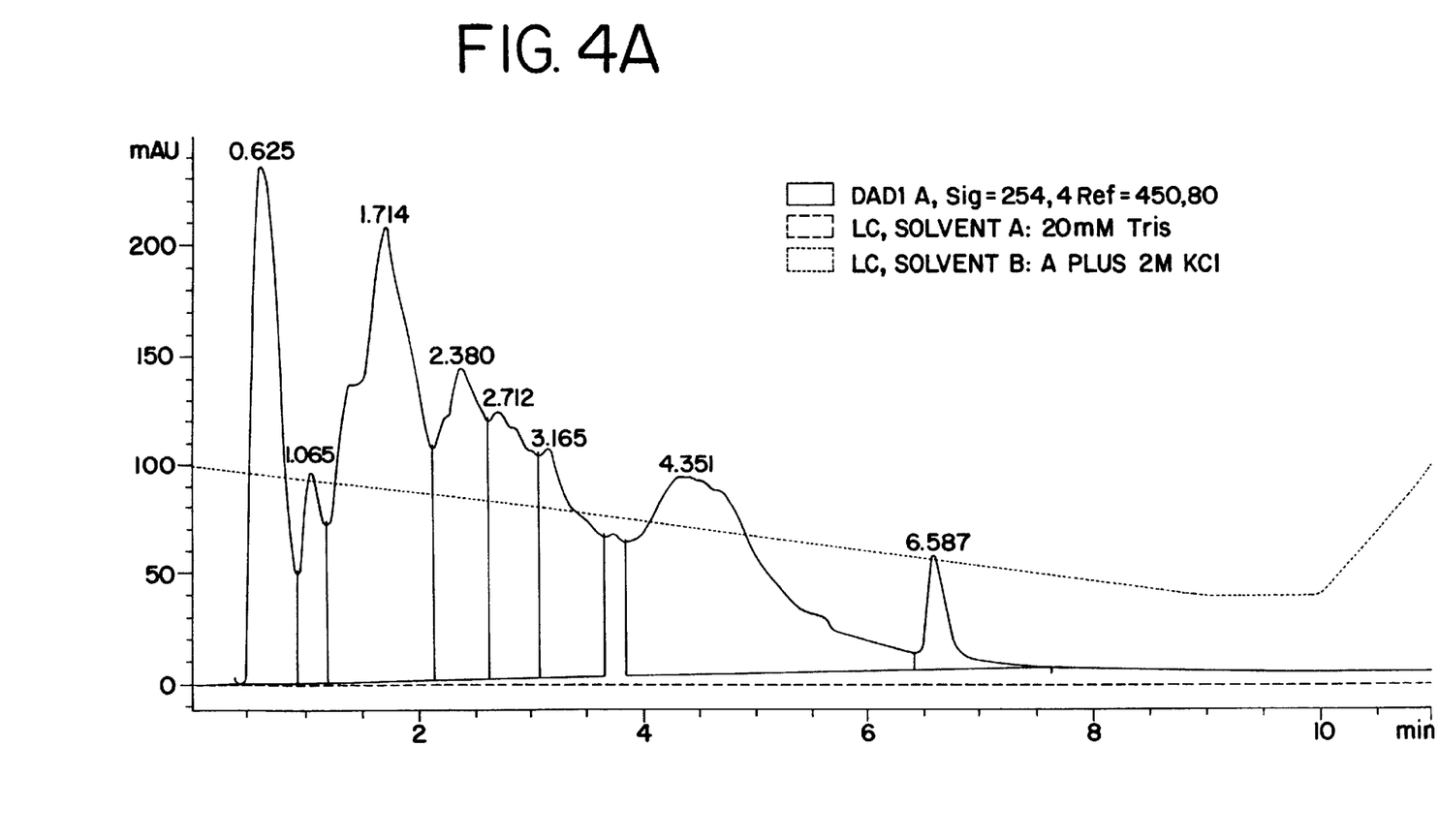
FIG. 4 is a graph of HPLC analyses of a p4119 preparation before TFU (Panel A) and the retentate fraction obtained after TFU (Panel B) as described in Example 1.
Figure 4B:
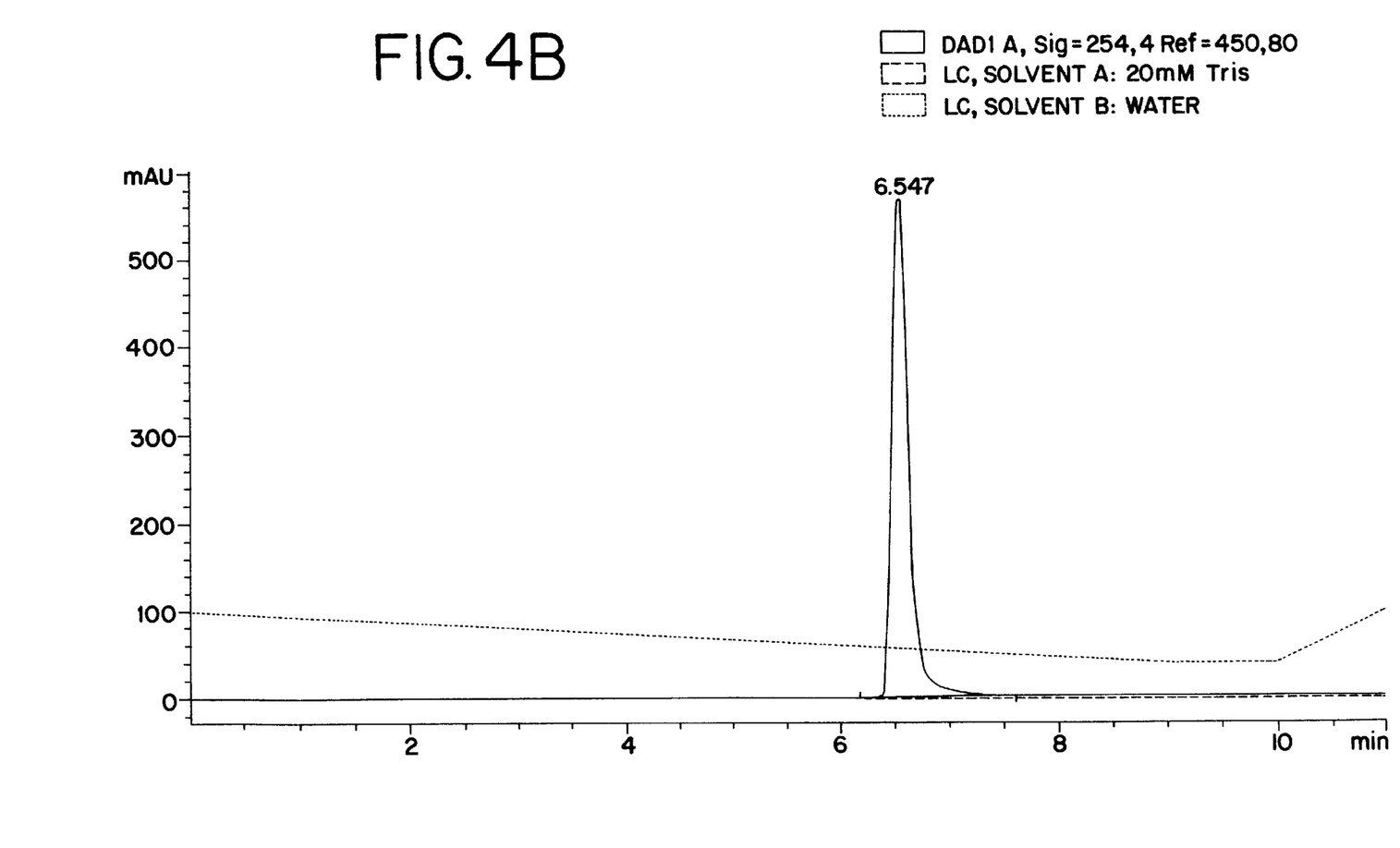

HPLC analyses were performed on a 4.6 mm×3.5 cm HPLC column packed with TSK-GEL DEAE-NPR resin at a buffer flow rate of 1 ml/min and monitored at 254 nm. Samples were diluted 1:20 with Buffer A (20 mM Tris-HCl, pH 8) and injected onto the column in a volume of 25 μl. Sample was eluted in a gradient of 0% Buffer B (20 mM Tris-HCl, pH 8/2 M KCl): 100% Buffer A to 60% Buffer B: 40% Buffer A over 9 min. HPLC analysis of the permeate (Panel A) and retentate containing plasmid DNA product (Panel B) are shown in FIG. 4. Plasmid DNA is typically 95% pure, and often 100% pure as determined by HPLC at this stage.

Spectrophotometric analysis was performed at wavelengths of 250, 260, and 280 nm. Typical ratios for purified DNA are $OD_{260}/OD_{250} > 1.1$, and $OD_{260}/OD_{280} > 1.9$. A total of 2.307 g of plasmid DNA was isolated and purified in the above procedure, having $OD_{260}/OD_{250}$ of 1.1047 and $OD_{260}/OD_{280}$ of 1.9290.

The recovered plasmid DNA was filtered twice through a Gelman Ground Water Capsule 0.45 µm filter, followed by two filtrations through a Pall-Filtron Capsule $N_{66}$ 0.22 µm filter.

Plasmid DNA was further purified by ion exchange chromatography. DNA was loaded in a total volume of 4740 ml onto a Amicon Vantage A column packed with a 2.5 L bed volume of TMAE-650 (M) (trinethylamino ethyl) Fractogel (EM Separations, Gibbstown, N.J.). The column was equilibrated with Equilibration Buffer (50 mM Tris, pH 8.5) at a LFV (linear flow velocity) between 80–150 cm/hr at 0.7 bar column pressure. The DNA was loaded at 225 ml/min flow rate at 0.7 bar column pressure. The column was washed with 3 to 5 column volumes of Equilibration Buffer at 32–35 mS. DNA was eluted from the column over an elution gradient of from 32 mS to 59 mS or from 0.5 M NaCl to 1.5 M NaCl in 50 mM Tris, pH 8.5, at a flow rate of 225 ml/min and a column pressure of 0.55 bar. Fractions were collected in volumes of 130 to 1650 ml starting when the A was greater than 0.2 and ending when the $A_{260}$ was less than 0.2.

All fractions were analyzed by HPLC and LAL endotoxin assay. The results are shown in Table 1. A total of 2044 mg DNA was loaded onto the column and 1946 mg were recovered in a total volume of 6079 ml, a yield of 95.22%. Column fractions 2–10 were pooled (1905 mg DNA and $3.73 \times 10^5$ EU LPS in 5941 ml). Fractions to be pooled were chosen to provide the maximum yield of recovered DNA while minimizing the amount of contaminating lipopolysaccharide (LPS) in the preparation.

TABLE 1

| Fraction | DNA conc. (mg/ml) | Volume (ml) | Yield (mg) | LPS (EU/ml) | LPS/DNA (EU/mg) |
|---|---|---|---|---|---|
| 1 | 0.30042 | 137.59 | 41.33 | 263.7 | 878 |
| 2 | 1.04234 | 531.01 | 553.49 | 353.2 | 339 |
| 3 | 0.88851 | 501.18 | 445.30 | 103.2 | 116 |
| 4 | 0.62513 | 481.00 | 300.69 | 53.6 | 85.7 |
| 5 | 0.43912 | 529.82 | 232.65 | 38.8 | 88.4 |
| 6 | 0.26979 | 585.56 | 157.98 | 35.0 | 130 |
| 7 | 0.14750 | 526.13 | 77.60 | 15.3 | 104 |
| 8 | 0.08712 | 568.91 | 49.56 | 11.8 | 135 |
| 9 | 0.05810 | 603.83 | 35.08 | 9.12 | 157 |
| 10 | 0.03288 | 1613.78 | 53.06 | 6.49 | 197 |

The recovered DNA solution was filtered through a Pall Ultipor $N_{66}$ 0.2 µm filter. To reduce the salt content, the DNA solution was subjected to a final diafiltration step using a Pall.-Filtron Centramate open channel 100 K MWCO membrane (2.0 sq. ft.). The filtration unit and membrane were first equilibrated with 1 L of a solution of 10 mM Tris-HCl, pH8.0. The buffer is circulated across the membrane using a pump and a sterile reservoir bottle. The DNA solution was added with the permeate channel fully open, and the solution circulated for approximately 30 min at 10 psi. The DNA solution was then ultrafiltered until concentrated to a volume of approximately 100 ml. The concentrated solution was then diafiltered using continuous diafiltration against a solution of 10 mM Tris-HCl, pH 8, at 10 psi and permeate flow rate of 120 ml/min until the conductivity of the solution was decreased from an initial value of 35 mS to less than 1 mS (0.60) (buffer conductivity=0.53 mS). With the permeate valve closed, the retentate was then recirculated through the ultrafilter for 10 min. The retentate was then collected, and the membrane washed with three 100 ml washes of 10 M Tris-HCl, pH 8.0.

The DNA and endotoxin concentrations of the diafiltered DNA solution and each of the washes was determined as above. The retentate and first wash were pooled, yielding 1.366 g DNA at a concentration of 5.564 mg/ml, and 90.35 EU/ml or 16.24 EU/mg DNA. This DNA solution was filtered through a Millipore Millipak 40 0.22 µm filter, followed by filtration of an additional 25 ml of final diafiltration buffer, and the two solutions pooled to yield the final product.

Yield of final plasmid DNA product from the final ultrafiltration was 80%. The final product was then aliquotted and stored at −20° C. until use. The final product was determined to meet the following Quality Control specifications:

| | |
|---|---|
| Color | clear to slightly cloudy |
| Endotoxin | <100 EU/ml |
| Purity | >95% by HPLC |
| DNA homogeneity | >90% ccc (covalently closed circular) |
| RNA | <2% by analytical HPLC |
| ssDNA | <1% by analytical HPLC |
| Protein | <0.1% by analytical HPLC, silver stain and SDS-PAGE |
| Genomic DNA | <1% by analytical HPLC and Southern Blot |
| Conductivity | <1 mS |
| pH | 7–8.5 |

Figure 5:
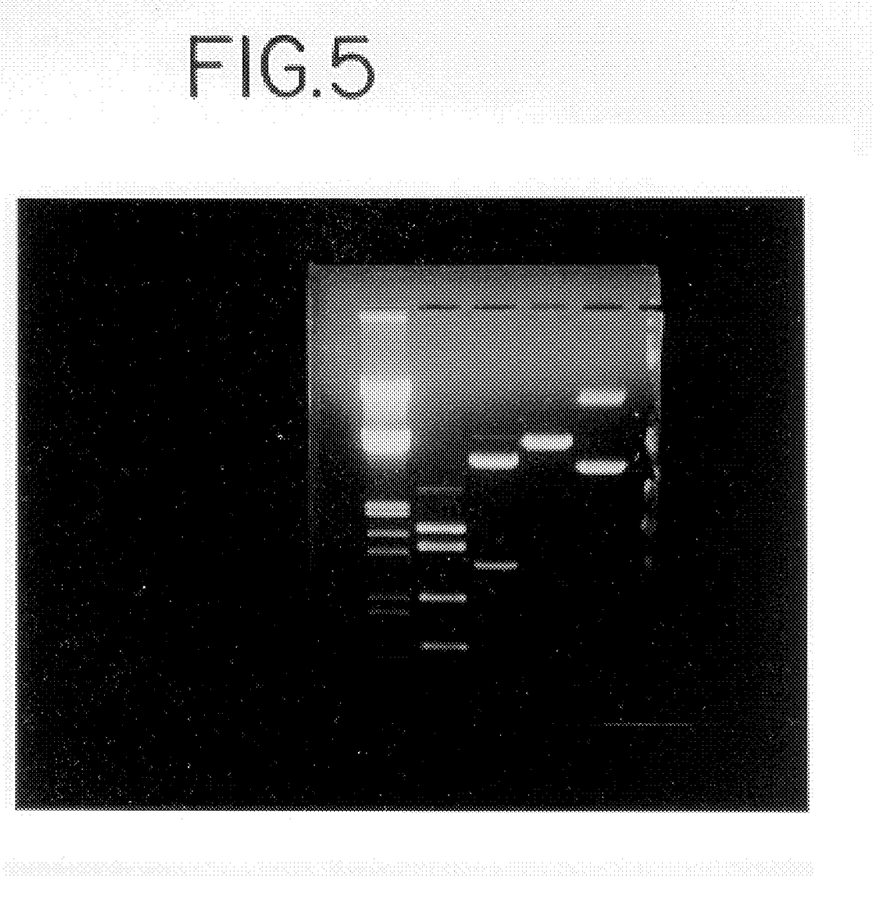
FIG. 5 shows the results of agarose gel electrophoresis of p4119 final purification product as described in Example 1. From left to right, the lanes are: (a) molecular weight markers, (b) p4119 cut four times, (c) p4119 cut two times, (d) p4119 cut one time, and (e) uncut p4119.
Figure 6:
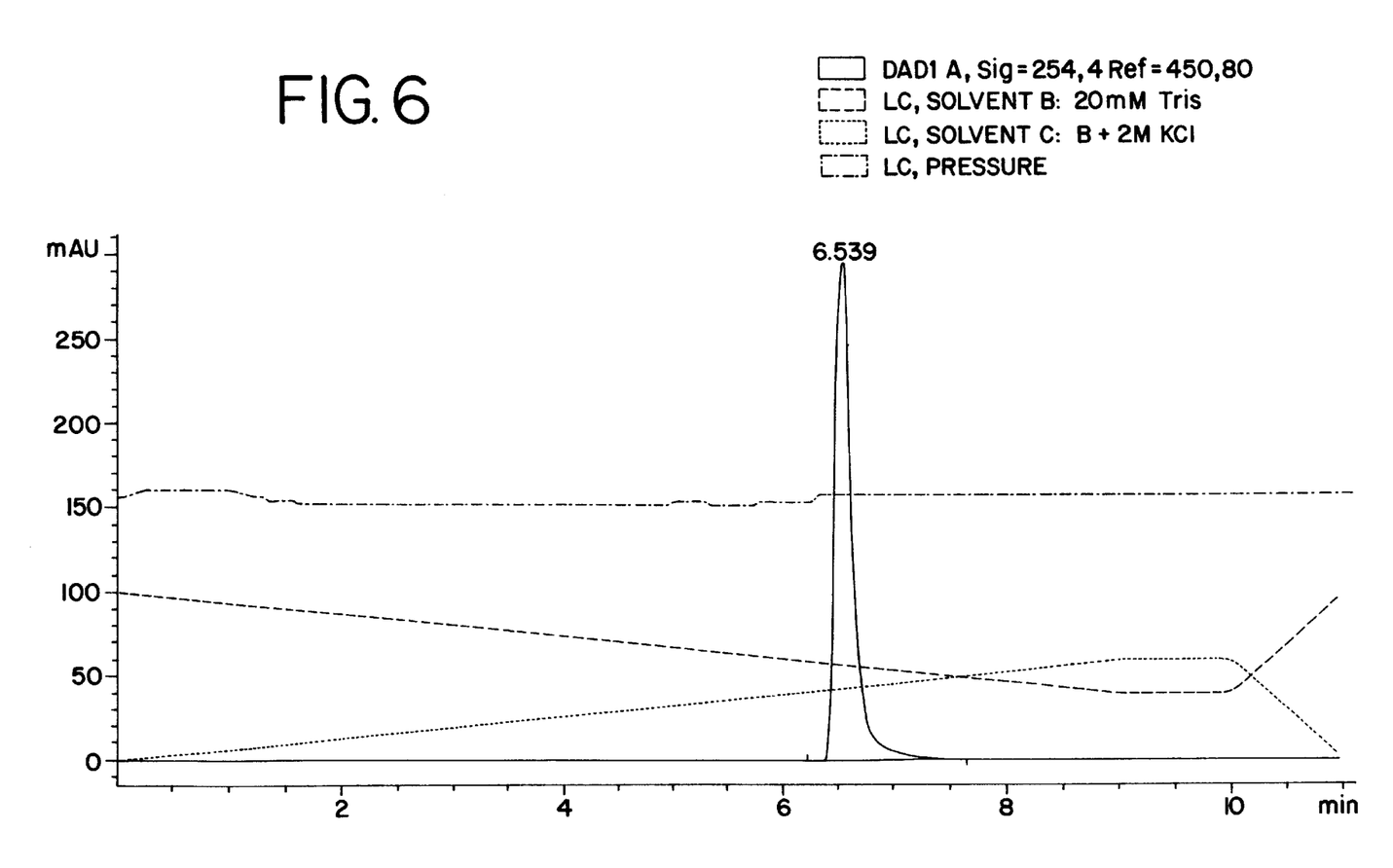
FIG. 6 is a graph of HPLC analysis of the final product of the p4119 purification described in Example 1.

Sterility was assayed by day 21 tryptose broth culture showing no colonies. Identity was determined by restriction endonuclease digestion and analysis by agarose gel electrophoresis. Results of the analysis of p4119 are shown in FIG. 5. HPLC analysis of the final product is shown in FIG. 6.

It will be understood by those with skill in the art that the degree of purity achieved using the methods of the present invention will depend on the intended uses of the purified nucleic acid. Accordingly, the invention is intended to encompass embodiments whereby any degree of purity, including the degree of purity illustrated by the examples herein, can be achieved. The invention is therefore not limited in scope to the use of the methods of the invention in their most optimal embodiments or to produce nucleic acid of the maximum obtainable purity.

It will be understood that the foregoing disclosure emphasizes certain specific embodiments of the invention and that all modifications and alternatives equivalent thereto are within the spirit and scope of the invention as set forth in the appended claims.

We claim:

1. A method for purifying a nucleic acid from a solution comprising the nucleic acid; the method comprising the steps of:
   a) circulating the solution through an ultrafiltration unit under conditions sufficient to allow a gel layer to form;
   b) filtering the solution through the ultrafiltration unit comprising a gel layer to provide a permeate solution and a retentate solution whereby the nucleic acid is retained in the retentate solution;
   c) collecting the retentate solution;
   whereby a purified nucleic acid solution is obtained.

2. The method of claim 1, wherein the nucleic acid is DNA.

3. The method of claim 1, wherein the nucleic acid is RNA.

4. The method of claim 2, wherein the DNA is plasmid DNA.

5. The method of claim 2, wherein the DNA is viral DNA.

6. The method of claim 3, wherein the RNA is viral RNA.

7. The method of claim 4, wherein the ultrafiltration unit comprises a membrane having a molecular weight cutoff of from about 100 K to about 500 K daltons.

8. The method of claim 1, wherein the gel layer is formed under pressure of from about 5 psi to about 30 psi.

9. The method of claim 1 wherein step (b) comprises concentrating the solution to provide a concentrated nucleic acid solution and diafiltering the concentrated nucleic acid solution with a diafiltration buffer.

10. The method of claim 9, further comprising circulating the diafiltration buffer through the ultrafiltration unit to provide a wash solution and combining the wash solution with the retentate solution.

11. The method of claim 1, further comprising the step of filtering the purified nucleic acid solution through a 0.2 µm filter.

12. The method of claim 11, further comprising the step of applying the purified nucleic acid solution to positively charged ion exchange chromatography resin wherein the nucleic acid is eluted from the ion exchange chromatography resin with a saline gradient to provide an eluted nucleic acid solution.

13. The method of claim 12, further comprising the step of reducing the conductivity of the eluted nucleic acid solution by diafiltration against a low-conductivity buffer.

14. The method of claim 1, wherein the purified nucleic acid solution comprises at least about 90% pure nucleic acid by HPLC.

15. The method of claim 4, wherein the purified nucleic acid solution comprises at least about 90% closed, circular plasmid DNA.

16. A method for purifying plasmid DNA from a solution comprising the nucleic acid, the method comprising the steps of:
   a) circulating the solution through an ultrafiltration unit comprising a membrane having a molecular weight cutoff in the range of from about 100 K to about 500 K daltons under conditions allowing a gel layer to form;
   b) filtering the solution through the ultrafiltration unit comprising a gel layer to provide a permeate solution and a retentate solution whereby the plasmid DNA is retained in the retentate solution;
   c) collecting the retentate solution to provide a purified plasmid DNA solution.

17. The method of claim 16, wherein the ultrafiltration membrane has a molecular weight cutoff of about 300 K.

18. The method of claim 16, wherein the solution comprising the nucleic acid is obtained from the lysis of bacterial cells using a detergent-containing buffer and the substantial removal of cellular debris and proteins.

19. The method of claim 16, further comprising diafiltering the solution to provide a volume exchange of from about 20 to about 100 volume equivalents of the retentate solution.

20. The method of claim 16, wherein the gel layer is formed using pressure of from about 5 psi to about 30 psi.

21. The method of claim 16, further comprising the step of filtering the purified plasmid DNA solution through a 0.2 µm filter.

22. The method of claim 16, further comprising the step of applying the purified nucleic acid solution to positively charged ion exchange chromatography resin wherein the nucleic acid is eluted from the ion exchange chromatography resin with a saline gradient to provide an eluted nucleic acid solution.

23. The method of claim 22, further comprising the step of reducing the conductivity of the eluted nucleic acid solution by diafiltration against a low-conductivity buffer.

24. A method for preparing purified plasmid DNA from a solution comprising the nucleic acid, the method the steps of:
   a) circulating the solution through an ultrafiltration unit comprising a membrane having a molecular weight cutoff of about 300 K daltons under pressure of from about 5 psi to about 30 psi for sufficient time to allow a gel layer to form;
   b) filtering the solution through the ultrafiltration unit comprising a gel layer to provide a retentate solution and a permeate solution whereby the plasmid DNA is retained in the retentate solution;
   c) diafiltering the retentate solution with a diafiltration buffer;
   d) collecting the retentate solution;
   e) washing the ultrafiltration membrane with the diafiltration buffer to provide a wash solution and adding the wash solution to the retentate solution to provide a combined retentate solution;
   f) filtering the combined retentate solution through a 0.2 µm filter to provide a substantially purified plasmid DNA solution;
   g) applying the substantially purified plasmid DNA solution to a positively charged ion exchange chromatography resin wherein the plasmid DNA is eluted from the ion exchange chromatography resin with a saline gradient to provide an eluted plasmid DNA solution;
   whereby a purified plasmid DNA solution is obtained.

25. The method of claim 24, wherein the solution comprising the nucleic acid is obtained from the lysis of bacterial cells using a detergent-containing buffer and the substantial removal of cellular debris and proteins.

26. A method for purifying plasmid DNA from a mixture of cells, comprising the steps of:
   a) disrupting the integrity of the cells comprising the mixture of cells in a detergent-containing buffer solution to provide a solubilized cell solution;
   b) enzymatically digesting cellular RNA in the solubilized cell solution;
   c) differentially precipitating cellular debris and proteins from nucleic acid in the solubilized cell solution to provide a supernatant solution comprising the nucleic acid;
   d) removing the precipitated cellular debris and proteins from the supernatant solution to provide a substantially purified plasmid DNA solution;
   e) further purifying the plasmid DNA by filtering the substantially purified plasmid DNA solution by tangential flow ultrafiltration to provide a permeate solution and a retentate solution whereby the plasmid DNA is retained in the retentate solution;
   f) collecting the retentate solution;
   whereby a purified plasmid DNA composition is obtained.

27. A method for purifying a nucleic acid from a solution comprising the nucleic acid, the method comprising:
   a) filtering the solution through an ultrafiltration unit comprising a gel layer to provide a permeate solution and a retentate solution whereby the nucleic acid is retained in the retentate solution, and
   b) collecting the retentate solution, whereby a purified nucleic acid solution is obtained.

28. The method of claim 27, wherein the nucleic acid is DNA.

29. The method of claim 27, wherein the nucleic acid is RNA.

30. The method of claim 28, wherein the DNA is plasmid DNA.

31. The method of claim 28, wherein the DNA is viral DNA.

32. The method of claim 29, wherein the RNA is viral RNA.

33. The method of claim 30, wherein the ultrafiltration unit comprises a membrane having a molecular weight cutoff of from about 50 k to about 500 k daltons.

34. The method of claim 27, wherein the ultrafiltration unit is an open-channel device.

35. The method of claim 34, wherein the ultrafiltration unit is flat-plate device.

36. The method of claim 34, wherein the ultrafiltration unit is a hollow fiber device.

37. The method of claim 27, wherein the gel layer is formed under pressure of from about 5 psi to about 30 psi.

38. The method claim 27, further comprising concentrating the solution to provide a concentrated nucleic acid solution, and diafiltering the concentrated nucleic acid solution with a diafiltration buffer.

39. The method of claim 36, further comprising circulating the diafiltration buffer through the ultrafiltration unit after collecting the retentate solution, to provide a wash solution and combining the wash solution with the retentate solution.

40. The method of claim 27, further comprising the step of filtering the purified nucleic acid solution through a 0.2 µm filter.

41. The method of claim 40, further comprising the step of applying the purified nucleic acid solution to a positively charged ion exchange chromatography resin wherein the nucleic acid is eluted from the ion exchange chromatography resin with a saline gradient to provide an eluted nucleic acid solution.

42. The method of claim 41, further comprising the step of diafiltering the eluted nucleic acid solution.

43. The method of claim 27, wherein the purified nucleic acid solution comprises at least about 90% pure nucleic acid.

44. The method of claim 30, wherein the purified nucleic acid solution comprises at least about 90% closed, circular plasmid DNA.

45. A method for purifying plasmid DNA from a solution comprising the plasmid DNA, the method comprising the steps of:
   a) filtering the solution through an open-channel ultrafiltration unit comprising a membrane having a molecular weight cutoff in the range of from about 50 K to about 500 K daltons to provide a permeate solution and a retentate solution, whereby the plasmid DNA is retained in the retentate solution; and
   b) collecting the retentate solution to provide a purified plasmid DNA solution.

46. The method of claim 45, wherein the filtering is performed in the presence of a gel layer.

47. The method of claim 45, wherein the ultrafiltration membrane has a molecular weight cutoff of about 300 K daltons.

48. The method of claim 45, wherein the solution comprising the plasmid DNA is obtained from the lysis of bacterial cells using a detergent-containing buffer and the substantial removal of cellular debris and proteins.

49. The method of claim 45, further comprising diafiltering the solution to provide a volume exchange of from about 10 to about 100 volume equivalents of the retentate solution.

50. The method of claim 46, wherein the gel layer is formed using pressure of from about 5 psi to about 30 psi.

51. The method of claim 45, further comprising the step of filtering the purified plasmid DNA solution through a 0.2 µm filter.

52. The method of claim 45, further comprising the step of applying the purified nucleic acid solution to positively charged ion exchange chromatography resin wherein the nucleic acid is eluted from the ion exchange chromatography resin with a saline gradient to provide an eluted nucleic acid solution.

53. The method of claim 52, further comprising the step of diafiltering the eluted nucleic acid solution against a low-conductivity buffer.

54. A method for preparing purified plasmid DNA from a solution comprising the plasmid DNA, the method comprising the steps of:
   a) circulating the solution through an open channel ultrafiltration unit comprising a membrane having a molecular weight cutoff of in the range of from about 300 K daltons to about 500 K daltons under pressure of from about 5 psi to about 30 psi for sufficient time to allow a gel layer to form;
   b) filtering the solution through the ultrafiltration unit comprising a gel layer to provide a retentate solution and a permeate solution whereby the plasmid DNA is retained in the retentate solution;
   c) diafiltering the retentate solution with a diafiltration buffer;
   d) collecting the retentate solution;
   e) filtering the combined retentate solution through a 0.2 µm filter to provide a substantially purified plasmid DNA solution;
   f) applying the substantially purified plasmid DNA solution to a positively charged ion exchange chromatography resin wherein the plasmid DNA is eluted from the ion exchange chromatography resin with a saline gradient to provide an eluted plasmid DNA solution;
   whereby a purified plasmid DNA solution is obtained.

55. The method of claim 54, wherein the solution comprising the plasmid DNA is obtained from the lysis of bacterial cells using a detergent-containing buffer and the substantial removal of cellular debris and proteins.

* * * * *